United States Patent [19]

Kadkhodayan

[11] Patent Number: 5,384,054
[45] Date of Patent: Jan. 24, 1995

[54] PROCESS FOR METAL SALTS OF HYDROCARBYL DITHIOPHOSPHORIC ACID

[75] Inventor: Abbas Kadkhodayan, Collinsville, Ill.

[73] Assignee: Ethyl Petrolium Additives, Inc., Richmond, Va.

[21] Appl. No.: 181,828

[22] Filed: Jan. 18, 1994

[51] Int. Cl.$^6$ .............................. C10M 1/48
[52] U.S. Cl. .................... 252/32.7 E; 252/18; 252/35; 252/49.9; 556/25
[58] Field of Search ............ 252/32.7 E, 18, 49.9, 252/32.7 R, 35; 556/25

[56] References Cited

U.S. PATENT DOCUMENTS

| | | | |
|---|---|---|---|
| 2,838,555 | 6/1958 | Goldsmith | 260/429.9 |
| 4,085,053 | 4/1978 | Caspari | 252/32.7 E |
| 4,123,370 | 10/1978 | Meinhardt | 252/32.7 E |
| 4,215,067 | 7/1980 | Brannen et al. | 260/429.9 |
| 4,263,150 | 4/1981 | Clason et al. | 252/32.7 E |

*Primary Examiner*—Prince Willis, Jr.
*Assistant Examiner*—Cephia D. Toomer

[57] ABSTRACT

This invention relates to a process for the production of overbased metal salts of hydrocarbyl dithiophosphoric acid comprising:

a) treating hydrocarbyl dithiophosphoric acid with an effective amount of phosphorus sulfide at a temperature within the range of from about 50° to about 200° C.; and b) neutralizing the treated hydrocarbyl dithiophosphoric acid with an amount of metal oxide;

whereby the effective amount of phosphorus sulfide is sufficient to form a basic metal salt of the dithiophosphoric acid having a base metal to phosphorus ratio within the range of from about 1.15:1 to about 1.3:1.

9 Claims, No Drawings

PROCESS FOR METAL SALTS OF HYDROCARBYL DITHIOPHOSPHORIC ACID

BACKGROUND

This invention relates to a process for the production of metal salts of hydrocarbyl dithiophosphoric acid particularly, overbased metal salts of hydrocarbyl dithiophosphoric acid.

It is well known that various additives can be used in lubricating oils in order to improve certain oil properties and to make a more satisfactory lubricant. For example, antiwear agents are intended to decrease wear of machine parts. Wear inhibitors for incorporation in motor oils and industrial oils are finding greater use as a result of greater stress placed on moving parts in high performance engines. Numerous other additives have been developed for use in such oil compositions to improve the lubricating characteristics thereof and thereby to lessen the wear of the moving parts.

Of the antiwear agents, the metal salts of hydrocarbyl dithiophosphoric acid, such as the diaryl and dialkyl dithiophosphates, especially zinc dithiophosphates, have long been used as antiwear additives and antioxidants in hydraulic oils, motor oils, automatic transmission fluids and the like. Processes for the production of metal salts of hydrocarbyl dithiophosphoric acid are well known. See U.S. Pat. Nos. 2,838,555; 3,848,032; 4,085,053; 4,123,370; 4,215,067; and 4,263,150 incorporated herein by reference. In a typical reaction, four equivalents of a hydroxy compound are reacted with phosphorus pentasulfide in the presence of a catalyst. Once formed, the hydrocarbyl dithiophosphoric acid is then separated from the reaction mass, and subsequently neutralized with an excess of metal base such as zinc oxide.

An important characteristic in determining the antiwear properties of the overbased metal salt of hydrocarbyl dithiophosphoric acid is the metal to phosphorus ratio. Typically, the metal to phosphorus ratio should be no less than about 1.15:1 and most preferably greater than about 1.20:1. However, variations in reactants and process conditions result in undesirable variations in the metal to phosphorus ratios of the products thus formed. If the metal salt of dithiophosphoric acid has too low a metal to phosphorus ratio, blending of the reaction product with a product having a higher metal to phosphorus ratio is required. It is desirable therefore to provide a process which will more consistently result in a clear reaction product having a metal to phosphorus ratio of no less than about 1.15:1.

THE INVENTION

A process has now been discovered which can be used to more consistently provide metal salts of hydrocarbyl dithiophosphoric acid having high metal to phosphorus ratios, e.g., metal to phosphorus ratios of no less than about 1.15:1. The process comprises:

(a) treating hydrocarbyl dithiophosphoric acid with an effective amount of phosphorus sulfide at a temperature within the range of from about 50° to about 200° C.; and (b) neutralizing the treated hydrocarbyl dithiophosphoric acid with an amount of metal oxide;

whereby the effective amount of phosphorus sulfide is sufficient to form a basic metal salt of the dithiophosphoric acid having a base metal to phosphorus ratio within the range of from about 1.15:1 to about 1.3:1.

While it is known to use phosphorus sulfide to prepare hydrocarbyl dithiophosphoric acid, it has been found, quite surprisingly and unexpectedly, that treatment of the intermediate hydrocarbyl dithiophosphoric acid product with an effective amount of additional phosphorus sulfide will result in an unexpected increase in the base metal to phosphorus ratio of the overbased metal salt of the hydrocarbyl dithiophosphoric acid reaction product. It is critical to the invention that the treatment be performed on the hydrocarbyl dithiophosphoric acid reaction product, i.e., after separation of the hydrocarbyl dithiophosphoric acid and excess reactants, one from the other, subsequent to the dithiophosphoric acid formation step.

In another embodiment, this invention provides a process for preparing an overbased metal salt of hydrocarbyl dithiophosphoric acid comprising:

a) reacting phosphorus sulfide and an alcohol in a first reaction mass in the presence of a catalytic amount of nitrogen containing catalyst thereby forming a hydrocarbyl dithiophosphoric acid;

b) separating the hydrocarbyl dithiophosphoric acid and first reaction mass, one from the other;

c) treating the hydrocarbyl dithiophosphoric acid with an effective amount of phosphorus sulfide at a temperature within the range of from about 50° to about 200° C.; and d) neutralizing the treated hydrocarbyl dithiophosphoric acid with an amount of metal oxide;

whereby the effective amount of phosphorus sulfide is sufficient to form a basic metal salt of the dithiophosphoric acid having a base metal to phosphorus ratio within the range of from about 1.15:1 to about 1.3:1.

The method for preparing the hydrocarbyl dithiophosphoric acid for reaction with a metal oxide is not critical to the invention and, thus, any of the well known processes for the thioacid formation reaction may be used. Generally, one mole of phosphorus pentasulfide ($P_2S_5$) is reacted in an agitated vessel with about four equivalents of alcohol in the presence of a nitrogen containing catalyst at a temperature within the range of from about 40° to about 120° C., most preferably about 100° to about 110° C. for alkyl alcohols having a boiling point higher than about 100° C. It is preferred to have an excess of alcohol present in the reaction mass, most preferably an excess of about 15 mole percent alcohol based on the number of moles of phosphorus sulfide reactant. Excess phosphorus sulfide in the reaction mass is generally avoided since when there is an excess of $P_2S_5$ in the reaction mass, there is a tendency to form excess quantities of hydrogen sulfide gas which must be removed and disposed of prior to the neutralization step.

The phosphorus sulfide reactant used in the thioacid formation and treatment steps of this invention may be selected from any one or more of $P_2S_3$, $P_2S_5$, $P_4S_7$, $P_4S_3$, $P_4S_9$, or mixtures of the foregoing with phosphorus pentasulfide being the most preferred. Such phosphorus sulfide compositions may contain minor amounts of free sulfur. While the structure of phosphorus pentasulfide is generally represented as $P_2S_5$ the actual structure is believed to contain four phosphorus atoms and ten sulfur atoms, i.e. $P_4S_{10}$. Accordingly, one mole of $P_4S_{10}$ will react with eight equivalents of hydroxy compound to produce the thioacid. For the purposes of this invention, the phosphorus sulfide reactant will be considered as containing a compound having the structure of $P_2S_5$ with the understanding that the actual structure is probably $P_4S_{10}$.

Subsequent to the thioacid formation reaction, a second reaction mass containing the hydrocarbyl dithiophosphoric acid product and $P_2S_5$ is formed for purposes of the treatment step. In the treatment step, the amount of $P_2S_5$ used to effect the purposes of this invention is generally within the range of from about 0.01 to about 4 wt. % based on the weight of thioacid to be treated. Accordingly, "the effective amount" of $P_2S_5$ is that amount sufficient to form a basic metal salt from the dithiophosphoric acid having a base metal to phosphorus ratio within the range of from about 1.15:1 to about 1.3:1. Preferred amounts of $P_2S_5$ range from about 0.05 to about 3 wt. %, with from about 0.08 to about 2 wt. % being particularly preferred.

During the treatment step, the hydrocarbyl dithiophosphoric acid product is heated in an agitated vessel to a temperature within the range of from about 50° to about 200° C., preferably from about 75° to about 150° C., and most preferably from about 80° to about 100° C. for a period of time ranging from about 10 minutes to about 10 hours. Typically, a treatment time of 30 minutes to 1 hour is sufficient for the purposes of this invention. Since there is a possibility of forming additional hydrogen sulfide in the treatment step, it is desirable to degas or sparge the second reaction mass with nitrogen during and subsequent to the treatment step.

At the termination of the treatment step, the treated hydrocarbyl dithiophosphoric acid is filtered to remove any solids remaining in the product and to separate the product and phosphorus pentasulfide, one from the other.

The hydroxy compounds from which the hydrocarbyl dithiophosphoric acids are derived can be represented generically by the formula ROH wherein R is hydrocarbyl or substituted hydrocarbyl group. Mixtures of hydroxy compounds may also be used. As is recognized in the art, these hydroxy compounds need not be monohydroxy compounds. That is, the hydrocarbyl dithiophosphoric acids may be prepared from mono-, di-, tri-, tetra-, and other polyhydroxy compounds, or mixtures of two or more of the foregoing.

Examples of the general class of compounds corresponding to the formula ROH are those wherein R is selected from an alkyl, cycloalkyl, alkyl-substituted cycloalkyl, aryl, alkaryl, arylalkyl, alkoxyalkyl, alkoxyaryl, haloalkyl, haloaryl, nitroaryl radical, and the like. Specific examples of such hydroxy compounds are phenol, resorcinol, hydroquinone, catechol, cresol, xylenol, hydroxydiphenyl, benzylphenol, phenylethylphenol, methylhydroxydiphenyl, guiacol, alpha- and beta-naphthol, alpha- and beta-methylnaphthol, tolylnaphthol, benzylnaphthol, anthranol, phenylmethylnaphthol, phenanthrol, monomethyl ether of catechol, anisole, chlorophenol, octyl alcohol, cyclohexanol, 2-ethylhexanol, isopropanol, methylcyclohexanol, cycloheptanol, cyclopentanol, 2,4-diamylphenoxyphenol, butanol, isoamyl alcohol, oleyl alcohol, dodecanol, lauryl alcohol, cetyl alcohol, ethylene glycol, propylene glycol, octylphenoxyethanol, methanol, ethyl alcohol, neopentyl alcohol, isohexyl alcohol, 2,3-dimethyl-butanol-1, n-heptanol, diisopropyl carbinol, glycerol, diethylene glycol, capryl alcohol, nonylphenol, decylphenol, and the like. Of the foregoing, the aliphatic alcohols and branched aliphatic alcohol are preferred. More preferred are the aliphatic alcohols having from 3 to 40 carbon atoms, most preferably 2-ethylhexanol. It is to be understood that most commercially available alcohols are not pure compounds but are, in fact, mixtures containing a predominant amount of the desired alcohol and minor amounts of various isomers and/or longer or shorter chain alcohols.

The dithiophosphoric acid formation reaction is typically conducted under substantially anhydrous conditions, in the absence of solvent, and in the presence of a catalytic amount of nitrogen containing catalyst. The nitrogen containing catalyst may be selected from $NH_3$ or a compound characterized by the presence within its structure of at least one group of the formula

wherein X is oxygen or a divalent sulfur atom. By "catalytic amount of catalyst" means that amount of catalyst which will provide the desired results in a given reaction for preparing a hydrocarbyl dithiophosphoric acid. Based on the total weight of $P_2S_5$ reactant used, the amount of catalyst will generally be within the range of from about 0.005% to about 1% by weight of $P_2S_5$ reactant. Illustrative nitrogen containing compounds containing the structure of the above formula include N-vinyl pyrrolidone, pyrrolidone, caprolactam, urea, thiourea, acetamide, benzamide, N,N-dimethylformamide, oleamide, linoleamide, or mixtures of two or more of the foregoing. The 5-, 6-, and 7-membered lactams are preferred catalysts with caprolactam being especially preferred.

Once the hydrocarbyl dithiophosphoric acid reaction is complete, the hydrocarbyl dithiophosphoric acid product may be stripped and cooled with an inert gas such as nitrogen to remove all traces of hydrogen sulfide. Any unreacted alcohol, $P_2S_5$ or other solids can be removed by decantation, filtration, or centrifugation.

The treated hydrocarbyl dithiophosphoric acid can be neutralized and overbased by contacting an aqueous slurry containing an excess of metal oxide with the treated hydrocarbyl dithiophosphoric acid. The amount of metal oxide used in the neutralization step is that amount sufficient to form the overbased metal salt of hydrocarbyl dithiophosphoric acid having a metal to phosphorus ratio of no less than about 1.15:1. Typically, an excess of metal oxide is used, preferably a molar excess of from about 10 to about 50%, more preferably, 15 to about 40%, and most preferably about 25 to 30%. The amount of water used to slurry the metal oxide is generally within the range of from about 5 to 10 moles of water per mole of metal oxide.

The neutralization reaction is generally carried out at elevated temperatures, e.g., temperatures within the range of from about 40° to about 130° C., preferably from about 50° to about 110° C., and most preferably from about 65° to about 90° C. Contacting of the treated hydrocarbyl dithiophosphoric acid with the metal oxide slurry is performed for a period of time sufficient to neutralize the acid and incorporate an excess amount of the metal oxide such that the material is effectively overbased.

The basic metal salts of hydrocarbyl dithiophosphoric acid useful in the neutralization step include the aluminum, tin, cobalt, lead, molybdenum, zinc, barium, calcium, strontium, chromium, iron, cadmium, magnesium, or nickel salts of hydrocarbyl dithiophosphoric acid made by neutralization of hydrocarbyl dithiophosphoric acid with aluminum, tin, cobalt, lead, molybdenum, zinc, barium, calcium, strontium, chromium, iron, cadmium, magnesium or nickel base. Of the basic metals, zinc oxide is preferred with high surface area zinc oxide being the most preferred. By "high surface area" means that the zinc oxide has a surface area of greater than about 3 m² per gram, preferably from about 5 to about 10 m² per gram.

In order to further illustrate the advantages of this invention, the following illustrative examples are given.

EXAMPLE 1

Preparation of di-2-ethylhexyl-dithiophosphoric acid

Into a 1 liter, 3-neck stirred glass reactor having a thermometer and temperature controlled heating mantle and $H_2S$ exhaust means were placed 0.2 grams (1.77 mmols) of caprolactam and 135.1 grams (1.04 mols) of 2-ethylhexanol. Phosphorus pentasulfide, 222.3 grams (0.5 mols) was transferred into a dry 500 mL round bottom flask. The reactor contents were heated to 65° C. and the phosphorus pentasulfide was added over a one hour period into the reactor using a collapsible rubber tube connection. The temperature of the reactor contents was allowed to rise to 75°–80° C. during the phosphorus pentasulfide addition. At the end of the phosphorus pentasulfide addition, 405.4 grams (3.1 mols) of 2-ethylhexanol was added to the reactor over a 2.5 hour period using an addition funnel while maintaining the temperature between 84°–88° C. Subsequent to the alcohol addition, the reaction mass was cooked for 1.5 hours at 84°–88° C. The entire reaction was conducted under a nitrogen pressure in order to prevent the escape of $H_2S$. Upon completion of the cook period, the reaction mass was filtered and the di-2-ethylhexyl-dithiophosphoric acid was collected.

EXAMPLE 2

Phosphorus pentasulfide treatment

To a 1-liter flask equipped with an agitator, thermometer, and reflux condenser was charged 600 grams (1.7 mols) of di-2-ethylhexyl-dithiophosphoric acid. To the acid was added 0.48 grams (2.1 mmols) of phosphorus pentasulfide. The reactor contents were then heated to 90° C. for 45 minutes under agitation. Upon completion of the phosphorus pentasulfide treatment, the reactor contents were filtered and nitrogen gas was bubbled through the treated dithiophosphoric acid for 30 minutes while maintaining the temperature of the acid at 60° C. to remove any traces of hydrogen sulfide. The thioacid was then neutralized with zinc oxide according to the procedure of Example 3.

EXAMPLE 3

Preparation of overbased zinc di-2-ethylhexyldithiophosphate

Into a 1-liter glass reaction vessel having a 1liter baffle, a four blade 45° pitch agitator, a thermometer and a heating mantle was charged 150.9 grams (8.38 mols) of water. The reactor contents were heated to 65° C. and the agitator was set at 700 rpm. Once the agitation rate was set, zinc oxide (77.4 grams, 0.95 mols) was charged to the reactor. Next 600 grams (1.7 mols) of di-2-ethylhexyl-dithiophosphoric acid from either Example 1 or Example 2 was charged to a 1000 mL pressure equalizing graduated funnel which was connected to the reactor using a glass offset adaptor. Vacuum was applied to the reactor vessel at 254 mm of Hg. When the temperature of the reactor contents obtained 65° C., the thioacid addition was begun and the temperature controller for the heating mantle was set at 75°–80° C. The thioacid was added to the reaction vessel over a 1 hour time period while maintaining the preset temperature and vacuum of 254 mm Hg. Once all of the acid was charged, the reactor contents were cooked for 1 hour at 75°–80° C. and 254 mm Hg vacuum. At the end of the cook period, the temperature controller was set at 85°–90° C. and the vacuum was raised to between 430 and 530 mm Hg so as to attain a dehydration rate of approximately 1 mL of distillate per minute and to maintain a temperature between 75°–79° C. The vacuum and dehydration temperatures were maintained for about 3 hours while monitoring the temperature of the reactor contents. At the end of the dehydration step, as indicated by a sharp rise in the reactor contents temperature, the vacuum was increased to 711 mm Hg and the temperature increased to 85°–90° C. for a one hour final cook period. After the final cook period, the product was filtered using 2.5 grams of filter aid, #2 qualitative 5.5-cm filter paper, and a vacuum filter funnel.

Comparisons of zinc di-2-ethylhexyldithiophosphate (ZDDP) made generally in accordance with Example 3 with and without the treatment step of Example 2 are given in the following tables.

TABLE 1

| | ZDDP without $P_2S_5$ treatment | ZDDP with $P_2S_5$ treatment |
|---|---|---|
| Wt. % zinc | 8.00 | 9.34 |
| Wt. % phosphorus | 7.86 | 7.92 |
| Viscosity at 40° C. (in centistokes) | 180 | 336 |
| Total Base Number (TBN in mg eq KOH/g) | 0 | 7.86 |
| pH | 3.96 | 6.42 |
| Zn/P ratio | 1.02 | 1.18 |

TABLE 2

| | ZDDP without $P_2S_5$ treatment | ZDDP with $P_2S_5$ treatment |
|---|---|---|
| Wt. % zinc | 7.87 | 9.11 |
| Wt. % phosphorus | 7.86 | 7.87 |
| Viscosity at 40° C. (in centistokes) | 136 | 300 |
| Total Base Number (TBN in mg eq KOH/g) | 0 | 5.49 |
| pH | 3.05 | 6.19 |
| Zn/P ratio | 1.00 | 1.16 |

TABLE 3

| | ZDDP without $P_2S_5$ treatment | ZDDP with $P_2S_5$ treatment |
|---|---|---|
| Wt. % zinc | 8.04 | 9.06 |
| Wt. % phosphorus | 7.96 | 7.91 |
| Viscosity at 400° C. (in centistokes) | 155 | 357 |
| Total Base Number (TBN in mg eq KOH/g) | 0 | 9.33 |
| pH | 3.89 | 6.18 |
| Zn/P ratio | 1.01 | 1.15 |

As can be seen from the foregoing examples, there is a significant increase in the zinc to phosphorus ratio for metal salt products of dithiophosphoric acid that have been treated with P$_2$S$_5$ prior to the neutralization and overbasing step.

Accordingly, the invention is subject to considerable variation within the spirit and scope of the appended claims.

What is claimed is:

1. A process for preparing an overbased metal salt of hydrocarbyl dithiophosphoric acid comprising:
   a) reacting phosphorus sulfide and an alcohol in a first reaction mass in the presence of a catalytic amount of nitrogen containing catalyst thereby forming a hydrocarbyl dithiophosphoric acid;
   b) separating the hydrocarbyl dithiophosphoric acid and first reaction mass, one from the other;
   c) treating the hydrocarbyl dithiophosphoric acid with an effective amount of phosphorus sulfide at a temperature within the range of from about 50° to about 200° C.; and
   d) neutralizing the treated hydrocarbyl dithiophosphoric acid with an amount of metal oxide; whereby the effective amount of phosphorus sulfide is sufficient to form a basic metal salt of the dithiophosphoric acid having a base metal to phosphorus ratio within the range of from about 1.15:1 to about 1.3:1.

2. The process of claim 1 wherein the metal oxide is zinc oxide.

3. The process of claim 2 wherein the alcohol is an aliphatic alcohol.

4. The process of claim 3 wherein the aliphatic alcohol contains from 3 to 40 carbon atoms.

5. The process of claim 3 wherein the aliphatic alcohol is 2-ethylhexanol.

6. The process of claim 1 wherein the effective amount of phosphorus sulfide ranges from about 0.01 to about 4.0 wt. % of the hydrocarbyl dithiophosphoric acid to be treated.

7. The process of claim 5 wherein the effective amount of phosphorus sulfide ranges from about 0.01 to about 4.0 wt. % of the hydrocarbyl dithiophosphoric acid to be treated.

8. The process of claim 1 wherein the phosphorus sulfide is phosphorus pentasulfide.

9. The process of claim 7 wherein the phosphorus sulfide is phosphorus pentasulfide.

* * * * *